United States Patent [19]
Takahashi et al.

[11] Patent Number: 5,705,129
[45] Date of Patent: Jan. 6, 1998

[54] NOX SENSOR

[75] Inventors: Tomonori Takahashi, Chita; Naoyuki Ogawa, Nagoya; Toshihiro Yoshida, Nagoya; Yuji Katsuda, Nagoya, all of Japan

[73] Assignee: NGK Insulators, Ltd., Japan

[21] Appl. No.: 626,314

[22] Filed: Apr. 2, 1996

[30] Foreign Application Priority Data

Apr. 10, 1995 [JP] Japan ............... 7-084019

[51] Int. Cl.$^6$ .............................. G01N 27/04
[52] U.S. Cl. .................. 422/90; 422/83; 422/94; 422/95; 422/98; 436/116; 436/118; 436/133; 436/134; 436/149; 204/425; 204/426; 204/427; 205/781; 73/23.31
[58] Field of Search ............... 422/83, 90, 94, 422/95, 98; 436/116, 118, 149, 133, 134; 204/425, 426, 427; 205/781; 73/23.31

[56] References Cited

U.S. PATENT DOCUMENTS

| | | | |
|---|---|---|---|
| 3,874,171 | 4/1975 | Schmidt et al. | 60/276 |
| 3,974,040 | 8/1976 | Siebke et al. | 204/1 T |
| 4,233,033 | 11/1980 | Eifler et al. | 422/98 |
| 4,315,753 | 2/1982 | Bruckenstein et al. | 422/98 |
| 4,840,913 | 6/1989 | Logothetis et al. | 436/116 |
| 4,915,080 | 4/1990 | Nakaniwa et al. | 123/489 |
| 4,927,517 | 5/1990 | Mizutani et al. | 204/406 |
| 4,953,387 | 9/1990 | Johnson et al. | 73/25.03 |
| 4,957,705 | 9/1990 | Uchikawa | 422/94 |
| 5,314,828 | 5/1994 | Dalla Betta et al. | 436/116 |
| 5,445,796 | 8/1995 | Mori | 422/90 |
| 5,486,336 | 1/1996 | Dalla Betta et al. | 42/98 |

FOREIGN PATENT DOCUMENTS 6-222028  8/1994  Japan .

*Primary Examiner*—Robert J. Warden
*Assistant Examiner*—Sharidan Carrillo
*Attorney, Agent, or Firm*—Parkhurst, Wendel & Burr, L.L.P.

[57] ABSTRACT

An NOx sensor has the sensor element made of an oxide, the resistance of which is varied in response to an NOx component in a gas to be measured, and a measuring portion for measuring a resistance variation of the sensor element and for detecting an NOx concentration in the gas to be measured. A catalyst is arranged at an upstream side of a flow of the gas to be measured with respect reach to the sensor element, which makes a partial pressure ratio of $NO/NO_2$ reach to an equilibrium state and removes a CO component from the gas to be measured. A heater for adjusting a temperature is arranged at a position close to the sensor element, which maintains temperatures of the sensor element and the catalyst constant. An $O_2$ sensor is arranged at a position close to the sensor element so that the measuring portion can detect accurately the concentration of Nox in the measurement gas by reference to the resistance of the sensor element.

7 Claims, 2 Drawing Sheets

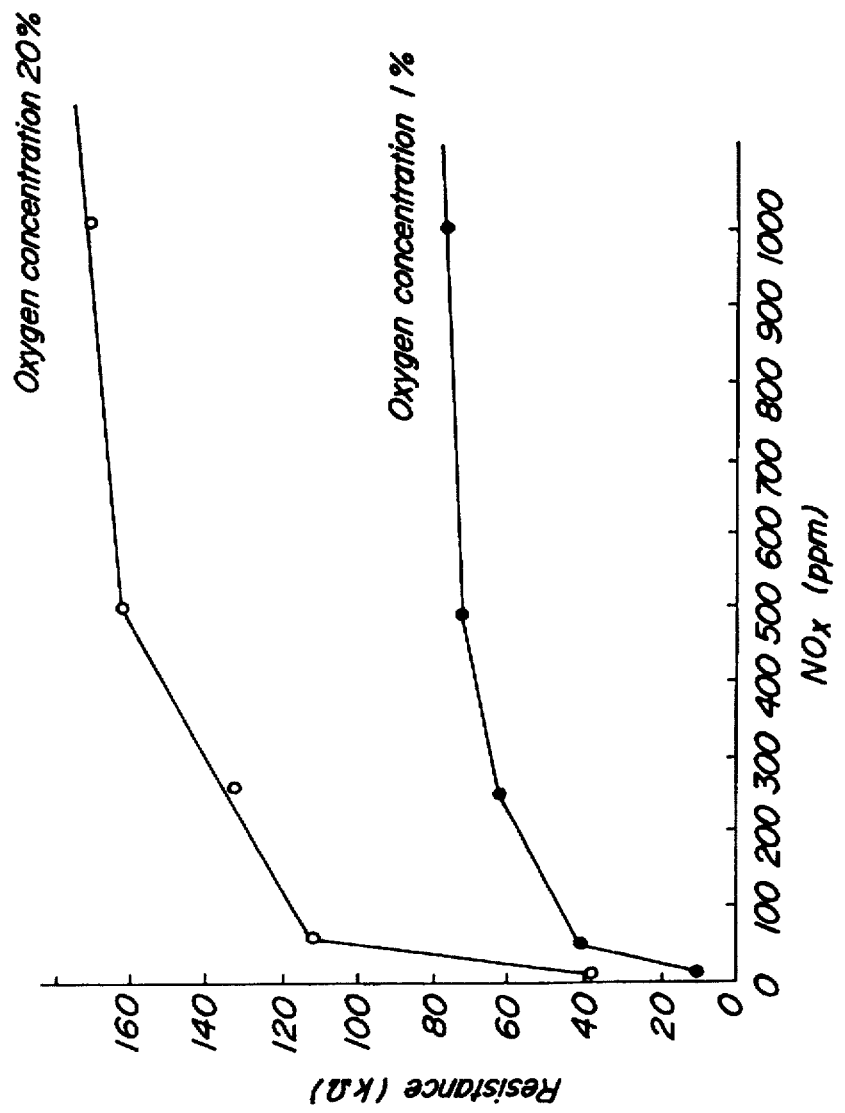

NOX SENSOR

BACKGROUND OF THE INVENTION

(1) Field of the Invention

The present invention relates to an NOx sensor having the sensor element made of an oxide, a resistance of which varies in response to an NOx component in a gas to be measured, and a measuring portion for measuring a resistance variation of the sensor element and for detecting an NOx concentration in the gas to be measured.

(2) Related Art Statement

As a method of measuring an NOx concentration in a gas to be measured such as a fired exhaust gas from an incinerator, which includes an NOx component such as nitrogen oxide, it is known to sample a gas to be measured including an NOx component, in for example, a dust chimney, and measure an NOx concentration of the sampled gas by means of an optical measuring apparatus. However, the optical measuring apparatus is expensive, and a responsible time thereof is long since the sampling operation is necessary.

In order to eliminate the drawbacks mentioned above, it has been proposed to use a direct insertion type semiconductor sensor, used recently. For example, in Japanese Patent Laid-Open Publication No. 6-222028, an NOx sensor comprising a response portion made of an oxide having a predetermined perovskite structure, and a conductivity measuring portion for measuring a conductivity of the response portion is disclosed.

However, also in the direct insertion type semiconductor sensor mentioned above, there is no countermeasure for an influence of $O_2$ and CO components included in the gas to be measured with respect to the measured NOx concentration. Moreover, in the response portion, the resistance thereof is varied in response to the concentration of NOx ($NO_2$+NO). However, if a ratio of concentration between $NO_2$ and NO a ratio of partial pressure between $NO_2$ and NO, is varied, a resistance measured by the response portion is varied even for the same NOx amount. In this case, it is reasonable to conclude that the NOx component is not selectively measured. Therefore, in the direct insertion type semiconductor sensor mentioned above, there is a drawback such that the NOx concentration in the gas to be measured cannot be selectively measured in a highly precise manner, while the semiconductor sensor is cheap and shows excellent response time as compared with the optical measuring apparatus.

SUMMARY OF THE INVENTION

An object of the present invention is to eliminate the drawbacks mentioned above and to provide an NOx sensor which can measure an NOx concentration in a gas to be measured selectively in a precise manner.

According to the invention, the NOx sensor has the sensor element made of an oxide, a resistance of which is varied in response to an NOx component in a gas to be measured, and a measuring portion for measuring a resistance variation of the sensor element and for detecting an NOx concentration in the gas to be measured. The sensor includes a catalyst arranged at an upstream side of a flow of the gas to be measured with respect to the sensor element, which maintains the partial pressure of NO and $NO_2$ in an equilibrium state and removes a CO component from the gas to be measured. A heater for adjusting temperature is arranged at a position close to the sensor element, and maintained the temperatures of the sensor element and the catalyst at a constant state. An $O_2$ sensor is arranged at a position close to the sensor element.

In the construction mentioned above, the gas to be measured passes through the catalyst which maintains the partial pressures of NO and $NO_2$ in an equilibrium state. The gas then the sensor element under such a condition that temperatures of the sensor element and the catalyst are maintained in a constant state by means of the heater. This arrangement makes it possible to perform a high precision measurement of NOx. That is to say, under such a condition mentioned above, a relation between a resistance measured by the sensor element and an NOx concentration is determined one by one in response to an $O_2$ concentration. Therefore, if the $O_2$ concentration is measured by the $O_2$ sensor for an adjustment and the NOx concentration is determined from the resistance value in response to the thus measured $O_2$ concentration, it is possible to perform a high precision measurement of NOx. Moreover, since the catalyst functions to remove a CO component from the gas to be measured, a CO component can be removed from the gas to be measured if the gas is contacted with the sensor element, and thus it is possible to measure the NOx concentration with no CO influence.

BRIEF DESCRIPTION OF THE DRAWING

FIG. 2 is a graph showing a relation between a resistance value measured in the NOx sensor and an NOx concentration according to the invention.

DESCRIPTION OF THE PREFERRED EMBODIMENTS

Figure 1:
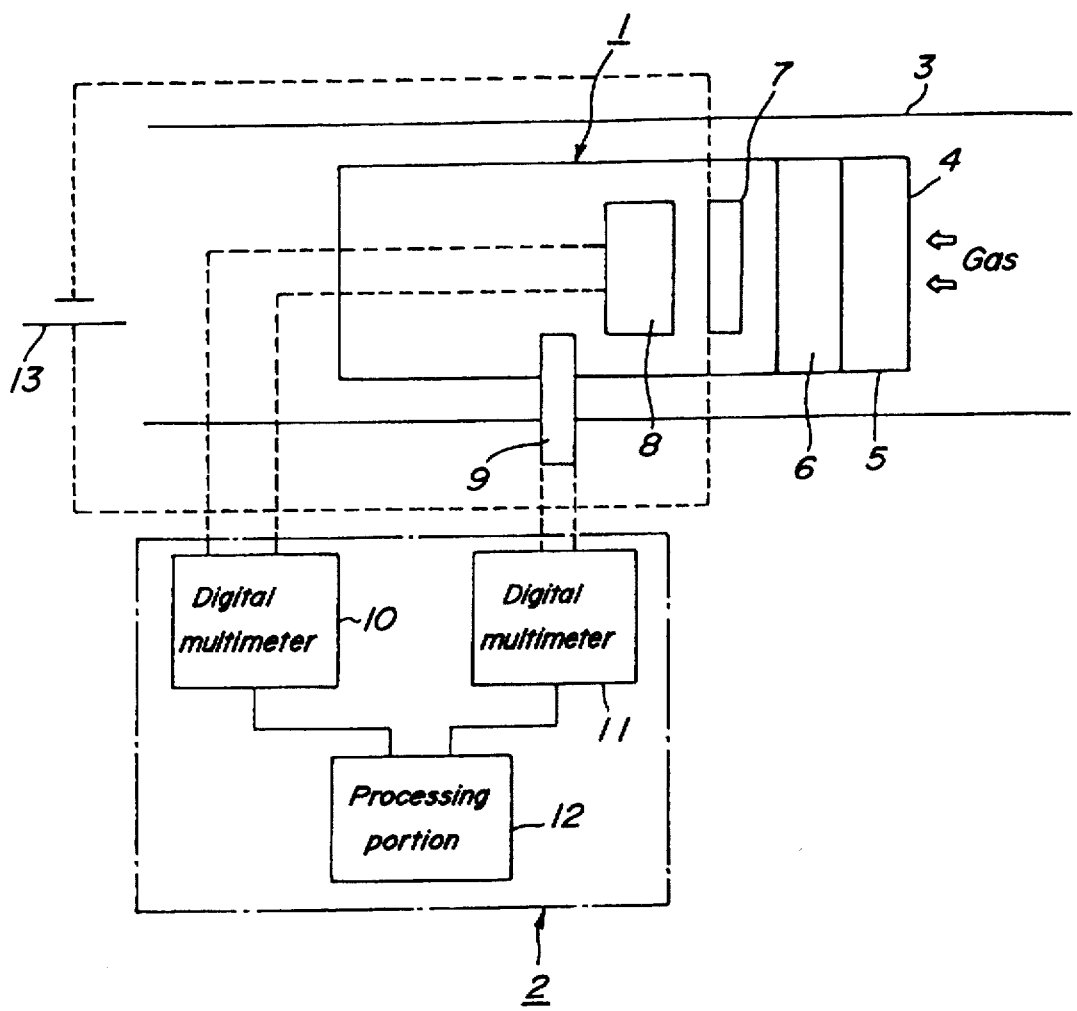
FIG. 1 is a schematic view for explaining one concept of an NOx sensor according to the invention.

FIG. 1 is a schematic view for explaining one concept of an NOx sensor according to the invention. In FIG. 1, an NOx sensor according to the invention comprises a response portion 1 and a measuring portion 2. The response portion 1 is set in a dust chimney 3 through which a gas to be measured flows. The response portion 1 is constructed by arranging, from an upstream side of a flow of the gas to be measured, a catalyst 6, heater 7 to control temperature of response portion 1 a sensor element 8 and an $O_2$ sensor 9, all of which are arranged in an alumina protection tube 5 having a gas inlet portion 4. The measuring portion 2 is constructed by arranging a digital multimeter 10 for the sensor element 8, a digital multimeter 11 for the $O_2$ sensor 9 and a processing portion 12. A constant-potential power supply 13 is provided for the heater.

The catalyst 6 is used to maintain the partial pressures of NO and $NO_2$ in an equilibrium state and for removing a CO component from the gas to be measured. In this embodiment, the catalyst 6 is integrally formed, but it is possible to form the catalyst 6 separately corresponding to the objects mentioned above, respectively. In the case of constructing the catalyst 6 separately, not only the same kinds of catalysts but also other kinds of catalysts may be used for the catalyst 6. In order to achieve the objects mentioned above, it is preferred to use precious metals or oxides as the catalyst 6. As the precious metals, it is preferred to use platinum, rhodium or gold. As the oxides, it is preferred to use manganese oxide, cobalt oxide or tin oxide.

The heater 7 is used for maintaining the sensor element 8 and the catalyst 6 at a constant temperature even if a temperature of the gas to be measured varies. Therefore, it is preferred to arrange heater 7 between the sensor element 8 and the catalyst 6. The sensor element 8 is made of an oxide, the resistance of which varies in response to an NOx component, if the oxide is contacted to the gas to be measured including an NOx component. As the oxide mentioned above, it is preferred to use metal oxide semiconductors. Among them, it is further preferred to use $SnO_2$, $TiO_2$ or $In_2O_3$. If the sensor element 8 is made of the oxides mentioned above, it is possible to use the same structure, shape and so on as those of the known sensor element.

In the NOx sensor according to the invention having the construction mentioned above, an NOx concentration measuring is performed as follows. At first, the gas to be measured is supplied from the gas inlet portion 4 into the response portion 1 under such a condition that temperatures of the sensor element 8 and the catalyst 6 are maintained constantly by means of heater 7. The thus supplied gas is passed through the catalyst 6. When the gas to be measured is passed through the catalyst 6, the partial pressures of NO and $NO_2$ are forced to achieve equilibrium and a CO component in the gas to be measured is burnt. Therefore, the gas to be measured, in which the partial pressure ratio of $NO/NO_2$ is at an equilibrium state and a CO component is removed, can be contacted with the sensor element 8.

In this case, a relation between a resistance of the sensor element 8 and NOx concentration can be determined directly if an oxygen concentration is constant. However, the oxygen concentration in the gas to be measured is not constant in practice. Therefore, in the present invention, the $O_2$ sensor 9 is arranged in the response portion 1 so as to always measure the oxygen concentration, and the NOx concentration is obtained from a relation between the resistance of the sensor element 8 based on the oxygen concentration and the NOx concentration. As one example, a relation between resistances at the oxygen concentrations of 1% and 20% and NOx concentrations, which is based on the results in the following experiment 1 of sample Nos. 1–10, is shown by FIG. 2. In FIG. 2, the relation is shown only at the oxygen concentrations 1% and 20%. However, if relations at the other oxygen concentrations are measured beforehand, the NOx concentration can be measured by using the relation corresponding to the oxygen concentration measured by the $O_2$ sensor 9. As a result, the NOx concentration can be measured without being affected by the partial pressure ratio of $NO/NO_2$, the $O_2$ component, the CO component and the atmospheric temperature.

Hereinafter, an actual embodiment will be explained.

Experiment 1

As shown in FIG. 1, the NOx sensor was constructed by arranging the catalyst 6, the heater 7, the sensor element 8 and the $O_2$ sensor 9. The sensor element 8 was produced according to the following steps. At first, tin chloride was subjected to a hydrolysis by using an ammonia solution to obtain a dissolved solution. Then, the dissolved solution was separated by a filtering. After that, the thus separated dissolved solution was subjected to a pyrolysis at 600° C. for 2 hours to synthesize tin oxide powders. Then, the thus obtained tin oxide powders were mixed in a wet state in ethanol solution for 10 hours by using zirconia balls to obtain an tin oxide slurry for dipping. As a body of the sensor element 8, use was made of an alumina tube having a diameter of 1.5 mm and a length of 5 mm to which a platinum wire having a diameter of 3 mm was secured. Then, the body was dipped in the tin oxide slurry. After that, the thus dipped body was fired at 800° C. for 2 hours to obtain the sensor element 8.

Moreover, the heater for a temperature adjustment 7 was produced by working a platinum wire into a coil shape. Further, platinum powders were arranged on a cordierite honeycomb carrier by a wash-coat method. After that, the cordierite honeycomb carrier was fired at 500° C. for 2 hours to obtain the catalyst 6 which functions to control the partial pressure ratio of $NO/NO_2$ and remove the CO component. As the $O_2$ sensor 9, use was made of a zirconia $O_2$ sensor. The measurement was performed in such a manner that a resistance of the sensor element 8 and a current of the $O_2$ sensor 9 were detected respectively by the digital multimeters 10 and 11 via the platinum lead wires.

As shown in the following Table 1, the gas to be measured including NOx such as $NO_2$ and NO having a predetermined concentration as well as the other components such as $O_2$, $CO_2$, $H_2O$, CO and $N_2$ was prepared. In this case, a total of all components was 100%. Then, the thus prepared gas was flowed, under such a condition that a temperature of the sensor element 8 was maintained constantly, to measure a resistance of the sensor element 8 by using the NOx sensor having the construction mentioned above. Moreover, as a comparative example, a resistance of the sensor element 8 was measured in the same manner as the example mentioned above except that a temperature of the sensor element 8 was not controlled and the catalyst 6 was not used. The results are shown in Table 1.

TABLE 1

| Sample No. | Sensor temperature (°C.) | Atmosphere temperature (°C.) | $NO/NO_2$ catalyst | CO burning catalyst | $NO_2$ (ppm) | NO (ppm) | NOx (ppm) | $O_2$ (%) | $CO_2$ (%) | $H_2O$ (%) | CO (ppm) | $N_2$ | Resistance (kΩ) |
|---|---|---|---|---|---|---|---|---|---|---|---|---|---|
| Example of Present Invention | | | | | | | | | | | | | |
| 1 | 500 | 400 | Pt | Pt | 200 | 800 | 1000 | 1 | 10 | 7 | 0 | remainder | 76.1 |
| 2 | 500 | 400 | Pt | Pt | 100 | 400 | 500 | 1 | 10 | 7 | 0 | remainder | 72.0 |
| 3 | 500 | 400 | Pt | Pt | 50 | 200 | 250 | 1 | 10 | 7 | 0 | remainder | 66.5 |
| 4 | 500 | 400 | Pt | Pt | 10 | 40 | 50 | 1 | 10 | 7 | 0 | remainder | 41.2 |
| 5 | 500 | 400 | Pt | Pt | 2 | 8 | 10 | 1 | 10 | 7 | 0 | remainder | 10.0 |
| 6 | 500 | 400 | Pt | Pt | 200 | 800 | 1000 | 20 | 10 | 7 | 0 | remainder | 169.1 |
| 7 | 500 | 400 | Pt | Pt | 100 | 400 | 500 | 20 | 10 | 7 | 0 | remainder | 161.0 |
| 8 | 500 | 400 | Pt | Pt | 50 | 200 | 250 | 20 | 10 | 7 | 0 | remainder | 153.2 |
| 9 | 500 | 400 | Pt | Pt | 10 | 40 | 50 | 20 | 10 | 7 | 0 | remainder | 112.3 |
| 10 | 500 | 400 | Pt | Pt | 2 | 8 | 10 | 20 | 10 | 7 | 0 | remainder | 38.0 |
| 11 | 500 | 400 | Pt | Pt | 100 | 400 | 500 | 1 | 10 | 7 | 1000 | remainder | 71.8 |
| 12 | 500 | 400 | Pt | Pt | 50 | 200 | 250 | 1 | 10 | 7 | 1000 | remainder | 66.3 |

TABLE 1-continued

| Sample No. | Sensor temperature (°C.) | Atmosphere temperature (°C.) | NO/NO$_2$ catalyst | CO burning catalyst | NO$_2$ (ppm) | NO (ppm) | NOx (ppm) | O$_2$ (%) | CO$_2$ (%) | H$_2$O (%) | CO (ppm) | N$_2$ | Resistance (kΩ) |
|---|---|---|---|---|---|---|---|---|---|---|---|---|---|
| 13 | 500 | 400 | Pt | Pt | 200 | 800 | 1000 | 20 | 10 | 7 | 1000 | remainder | 168.8 |
| 14 | 500 | 400 | Pt | Pt | 100 | 400 | 500 | 1 | 10 | 7 | 0 | remainder | 72.1 |
| 15 | 500 | 400 | Pt | Pt | 100 | 400 | 500 | 1 | 10 | 20 | 0 | remainder | 72.0 |
| 16 | 500 | 400 | Pt | Pt | 40 | 10 | 50 | 1 | 10 | 7 | 0 | remainder | 41.0 |
| 17 | 500 | 400 | Pt | Pt | 800 | 200 | 1000 | 1 | 10 | 7 | 0 | remainder | 76.0 |
| 18 | 500 | 400 | Pt | Pt | 800 | 200 | 1000 | 20 | 10 | 7 | 0 | remainder | 170.0 |
| 19 | 500 | 300 | Pt | Pt | 200 | 800 | 1000 | 1 | 10 | 7 | 0 | remainder | 76.0 |
| 20 | 500 | 300 | Pt | Pt | 200 | 800 | 1000 | 20 | 10 | 7 | 0 | remainder | 169.7 |
| 21 | 500 | 300 | Pt | Pt | 800 | 200 | 1000 | 1 | 10 | 7 | 0 | remainder | 76.2 |
| Comparative Example | | | | | | | | | | | | | |
| 1 | not control | 400 | None | None | 200 | 800 | 1000 | 1 | 10 | 7 | 0 | remainder | 462.3 |
| 2 | not control | 400 | None | None | 200 | 800 | 1000 | 1 | 10 | 7 | 1000 | remainder | 91.2 |
| 3 | not control | 400 | None | None | 200 | 800 | 1000 | 20 | 10 | 7 | 0 | remainder | 997.5 |
| 4 | not control | 400 | None | None | 800 | 200 | 1000 | 1 | 10 | 7 | 0 | remainder | 534.8 |
| 5 | not control | 300 | None | None | 200 | 800 | 1000 | 1 | 10 | 7 | 0 | remainder | 1676 |

From the results shown in Table 1, when the oxygen concentration is constant, it is understood that the same resistance can be obtained consistently in the examples according to the invention even if a concentration ratio between NO$_2$ and NO is varied and also the CO component is included. On the other hand, it is understood that the resistances are largely varied in the comparative examples. Therefore, in the examples according to the invention, if the NOx concentration is measured from the resistance, the constant NOx concentration can be obtained consistently even if a concentration ratio between NO$_2$ and NO is varied and also the CO component is included. Accordingly, the precise measurement of NOx can be performed. On the other hand, in the comparative examples, even if the NOx concentration is measured from the resistance, the constant NOx concentration cannot be obtained, and thus the measurement accuracy is diminished.

Experiment 2

The NOx concentration measuring was performed in the same manner as that of the experiment 1 by using the substantially same NOx sensor as that of the experiment 1 except that an indium oxide obtained by subjecting a nitrate to a pyrolysis at 600° C. for 2 hours was used as a material of the sensor element 8, a manganese oxide was used as the catalyst 6 for controlling the partial pressure ratio of NO/NO$_2$, and a tin oxide was used as the catalyst 6 for removing the CO component. The results are shown in Table 2.

TABLE 2

| Sample No. | Sensor temperature (°C.) | Atmosphere temperature (°C.) | NO/NO$_2$ catalyst | CO burning catalyst | NO$_2$ (ppm) | NO (ppm) | NOx (ppm) | O$_2$ (%) | CO$_2$ (%) | H$_2$O (%) | CO (ppm) | N$_2$ | Resistance (kΩ) |
|---|---|---|---|---|---|---|---|---|---|---|---|---|---|
| Example of Present Invention | | | | | | | | | | | | | |
| 1 | 500 | 400 | Mn$_3$O$_4$ | SnO$_2$ | 200 | 800 | 1000 | 1 | 10 | 7 | 0 | remainder | 3.54 |
| 2 | 500 | 400 | Mn$_3$O$_4$ | SnO$_2$ | 100 | 400 | 500 | 1 | 10 | 7 | 0 | remainder | 3.11 |
| 3 | 500 | 400 | Mn$_3$O$_4$ | SnO$_2$ | 50 | 200 | 250 | 1 | 10 | 7 | 0 | remainder | 2.23 |
| 4 | 500 | 400 | Mn$_3$O$_4$ | SnO$_2$ | 10 | 40 | 50 | 1 | 10 | 7 | 0 | remainder | 1.10 |
| 5 | 500 | 400 | Mn$_3$O$_4$ | SnO$_2$ | 2 | 8 | 10 | 1 | 10 | 7 | 0 | remainder | 0.21 |
| 6 | 500 | 400 | Mn$_3$O$_4$ | SnO$_2$ | 200 | 800 | 1000 | 20 | 10 | 7 | 0 | remainder | 9.02 |
| 7 | 500 | 400 | Mn$_3$O$_4$ | SnO$_2$ | 100 | 400 | 500 | 20 | 10 | 7 | 0 | remainder | 8.34 |
| 8 | 500 | 400 | Mn$_3$O$_4$ | SnO$_2$ | 50 | 200 | 250 | 20 | 10 | 7 | 0 | remainder | 7.22 |
| 9 | 500 | 400 | Mn$_3$O$_4$ | SnO$_2$ | 10 | 40 | 50 | 20 | 10 | 7 | 0 | remainder | 3.12 |
| 10 | 500 | 400 | Mn$_3$O$_4$ | SnO$_2$ | 2 | 8 | 10 | 20 | 10 | 7 | 0 | remainder | 0.63 |
| 11 | 500 | 400 | Mn$_3$O$_4$ | SnO$_2$ | 100 | 400 | 500 | 1 | 10 | 7 | 1000 | remainder | 3.13 |
| 12 | 500 | 400 | Mn$_3$O$_4$ | SnO$_2$ | 50 | 200 | 250 | 1 | 10 | 7 | 1000 | remainder | 2.24 |
| 13 | 500 | 400 | Mn$_3$O$_4$ | SnO$_2$ | 200 | 800 | 1000 | 20 | 10 | 7 | 1000 | remainder | 9.04 |
| 14 | 500 | 400 | Mn$_3$O$_4$ | SnO$_2$ | 100 | 400 | 500 | 1 | 10 | 7 | 0 | remainder | 3.11 |
| 15 | 500 | 400 | Mn$_3$O$_4$ | SnO$_2$ | 100 | 400 | 500 | 1 | 10 | 20 | 0 | remainder | 3.12 |
| 16 | 500 | 400 | Mn$_3$O$_4$ | SnO$_2$ | 40 | 10 | 50 | 1 | 10 | 7 | 0 | remainder | 1.12 |
| 17 | 500 | 400 | Mn$_3$O$_4$ | SnO$_2$ | 800 | 200 | 1000 | 1 | 10 | 7 | 0 | remainder | 3.56 |
| 18 | 500 | 400 | Mn$_3$O$_4$ | SnO$_2$ | 800 | 200 | 1000 | 20 | 10 | 7 | 0 | remainder | 9.00 |
| 19 | 500 | 300 | Mn$_3$O$_4$ | SnO$_2$ | 200 | 800 | 1000 | 1 | 10 | 7 | 0 | remainder | 3.55 |
| 20 | 500 | 300 | Mn$_3$O$_4$ | SnO$_2$ | 200 | 800 | 1000 | 20 | 10 | 7 | 0 | remainder | 9.01 |
| 21 | 500 | 300 | Mn$_3$O$_4$ | SnO$_2$ | 800 | 200 | 1000 | 1 | 10 | 7 | 0 | remainder | 3.56 |

TABLE 2-continued

| Sample No. | Sensor temperature (°C.) | Atmosphere temperature (°C.) | NO/NO$_2$ catalyst | CO burning catalyst | NO$_2$ (ppm) | NO (ppm) | NOx (ppm) | O$_2$ (%) | CO$_2$ (%) | H$_2$O (%) | CO (ppm) | N$_2$ | Resistance (kΩ) |
|---|---|---|---|---|---|---|---|---|---|---|---|---|---|
| Comparative Example | | | | | | | | | | | | | |
| 1 | not control | 400 | None | None | 200 | 800 | 1000 | 1 | 10 | 7 | 0 | remainder | 18.54 |
| 2 | not control | 400 | None | None | 200 | 800 | 1000 | 1 | 10 | 7 | 1000 | remainder | 5.50 |
| 3 | not control | 400 | None | None | 200 | 800 | 1000 | 20 | 10 | 7 | 0 | remainder | 46.98 |
| 4 | not control | 400 | None | None | 800 | 200 | 1000 | 1 | 10 | 7 | 0 | remainder | 24.38 |
| 5 | not control | 300 | None | None | 200 | 800 | 1000 | 1 | 10 | 7 | 0 | remainder | 35.46 |

Also from the results shown in Table 2, when the oxygen concentration is constant, it is understood that the same resistance can be obtained consistently in the examples according to the invention even if a concentration ratio between NO$_2$ and NO is varied and also the CO component is included. On the other hand, it is understood that the resistances are largely varied in the comparative examples.

Experiment 3

The NOx concentration measuring was performed in the same manner as that of the experiment 1 by using the substantially same NOx sensor as that of the experiment 1 except that a titanium oxide obtained by subjecting a sulfate to a pyrolysis at 800° C. for 1 hour was used as a material of the sensor element 8, a cobalt oxide was used as the catalyst 6 for controlling the partial pressure ratio of NO/NO$_2$, and gold was used as the catalyst 6 for removing the CO component. The results are shown in Table 3.

Also from the results shown in Table 3, when the oxygen concentration is constant, it is understood that the same resistance can be obtained consistently in the examples according to the invention even if a concentration ratio between NO$_2$ and NO is varied and also the CO component is included. On the other hand, it is understood that the resistances are largely varied in the comparative example.

As clearly understood from the above, according to the invention, since the gas to be measured passed through the catalyst which makes a partial pressure ratio of NO/NO$_2$ reach an equilibrium state is contacted to the sensor element under such a condition that temperatures of the sensor element and the catalyst are maintained in a constant state by means of the heater, it is possible to perform a high precision measurement. That is to say, under such a condition mentioned above, a relation between a resistance measured by the sensor element and an NOx concentration is determined

TABLE 3

| Sample No. | Sensor temperature (°C.) | Atmosphere temperature (°C.) | NO/NO$_2$ catalyst | CO burning catalyst | NO$_2$ (ppm) | NO (ppm) | NOx (ppm) | O$_2$ (%) | CO$_2$ (%) | H$_2$O (%) | CO (ppm) | N$_2$ | Resistance (kΩ) |
|---|---|---|---|---|---|---|---|---|---|---|---|---|---|
| Example of Present Invention | | | | | | | | | | | | | |
| 1 | 500 | 400 | Co$_3$O$_4$ | Au | 200 | 800 | 1000 | 1 | 10 | 7 | 0 | remainder | 23611 |
| 2 | 500 | 400 | Co$_3$O$_4$ | Au | 100 | 400 | 500 | 1 | 10 | 7 | 0 | remainder | 19872 |
| 3 | 500 | 400 | Co$_3$O$_4$ | Au | 50 | 200 | 250 | 1 | 10 | 7 | 0 | remainder | 15181 |
| 4 | 500 | 400 | Co$_3$O$_4$ | Au | 10 | 40 | 50 | 1 | 10 | 7 | 0 | remainder | 6429 |
| 5 | 500 | 400 | Co$_3$O$_4$ | Au | 2 | 8 | 10 | 1 | 10 | 7 | 0 | remainder | 760 |
| 6 | 500 | 400 | Co$_3$O$_4$ | Au | 200 | 800 | 1000 | 20 | 10 | 7 | 0 | remainder | 56262 |
| 7 | 500 | 400 | Co$_3$O$_4$ | Au | 100 | 400 | 500 | 20 | 10 | 7 | 0 | remainder | 47351 |
| 8 | 500 | 400 | Co$_3$O$_4$ | Au | 50 | 200 | 250 | 20 | 10 | 7 | 0 | remainder | 36201 |
| 9 | 500 | 400 | Co$_3$O$_4$ | Au | 10 | 40 | 50 | 20 | 10 | 7 | 0 | remainder | 15210 |
| 10 | 500 | 400 | Co$_3$O$_4$ | Au | 2 | 8 | 10 | 20 | 10 | 7 | 0 | remainder | 1811 |
| 11 | 500 | 400 | Co$_3$O$_4$ | Au | 100 | 400 | 500 | 1 | 10 | 7 | 1000 | remainder | 19869 |
| 12 | 500 | 400 | Co$_3$O$_4$ | Au | 50 | 200 | 250 | 1 | 10 | 7 | 1000 | remainder | 15182 |
| 13 | 500 | 400 | Co$_3$O$_4$ | Au | 200 | 800 | 1000 | 20 | 10 | 7 | 1000 | remainder | 56259 |
| 14 | 500 | 400 | Co$_3$O$_4$ | Au | 100 | 400 | 500 | 1 | 10 | 7 | 0 | remainder | 19870 |
| 15 | 500 | 400 | Co$_3$O$_4$ | Au | 100 | 400 | 500 | 1 | 10 | 20 | 0 | remainder | 19874 |
| 16 | 500 | 400 | Co$_3$O$_4$ | Au | 40 | 10 | 50 | 1 | 10 | 7 | 0 | remainder | 6430 |
| 17 | 500 | 400 | Co$_3$O$_4$ | Au | 800 | 200 | 1000 | 1 | 10 | 7 | 0 | remainder | 23613 |
| 18 | 500 | 400 | Co$_3$O$_4$ | Au | 800 | 200 | 1000 | 20 | 10 | 7 | 0 | remainder | 56259 |
| 19 | 500 | 300 | Co$_3$O$_4$ | Au | 200 | 800 | 1000 | 1 | 10 | 7 | 0 | remainder | 23610 |
| 20 | 500 | 300 | Co$_3$O$_4$ | Au | 200 | 800 | 1000 | 20 | 10 | 7 | 0 | remainder | 56263 |
| 21 | 500 | 300 | Co$_3$O$_4$ | Au | 800 | 200 | 1000 | 1 | 10 | 7 | 0 | remainder | 23616 |
| Comparative Example | | | | | | | | | | | | | |
| 1 | not control | 400 | None | None | 200 | 800 | 1000 | 1 | 10 | 7 | 0 | remainder | 35125 |
| 2 | not control | 400 | None | None | 200 | 800 | 1000 | 1 | 10 | 7 | 1000 | remainder | 3864 |
| 3 | not control | 400 | None | None | 200 | 800 | 1000 | 20 | 10 | 7 | 0 | remainder | 87540 |
| 4 | not control | 400 | None | None | 800 | 200 | 1000 | 1 | 10 | 7 | 0 | remainder | 98734 |
| 5 | not control | 300 | None | None | 200 | 800 | 1000 | 1 | 10 | 7 | 0 | remainder | 78654 | directly in response to an $O_2$ concentration. Therefore, if the $O_2$ concentration is measured by the $O_2$ sensor for an adjustment and the NOx concentration is determined from the resistance value in response to the thus measured $O_2$ concentration, it is possible to perform a high precision measurement. Moreover, since the catalyst functions to remove a CO component from the gas to be measured, a CO component can be removed from the gas to be measured if the gas is contacted with the sensor element, and thus it is possible to measure the NOx concentration with no CO influence.

What is claimed is:

1. An apparatus for sensing NOx in a measurement gas, comprising:

an oxide sensor element arranged in a flow path of the measurement gas, the resistance of said oxide sensor element varying in response to changes in NOx concentration of the measurement gas;

a catalyst arranged upstream of said oxide sensor element to maintain partial pressures of NO and $NO_2$ in the measurement gas at an equilibrium state and remove CO from the measurement gas;

heating means arranged proximate said oxide sensor element and said catalyst for maintaining the temperature of said oxide sensor element and said catalyst substantially constant;

an $O_2$ sensor arranged proximate said oxide sensor element for measuring the concentration of oxygen in the measurement gas; and measuring means for receiving signals from said oxide sensor element and said $O_2$ sensor and for determining the concentration of NOx in the measurement gas.

2. The apparatus of claim 1, wherein said measuring means detects the oxygen concentration of the measurement gas using said $O_2$ sensor, detects the resistance of said oxide sensor element, and determines the NOx concentration of the measurement gas based on the detected oxygen concentration and the detected resistance of said oxide sensor element.

3. The apparatus of claim 1, wherein said oxide sensor element comprises a metal oxide semiconductor.

4. The apparatus of claim 3, wherein said metal oxide semiconductor is selected from the group consisting of $SnO_2$, $TiO_2$ and $In_2O_3$.

5. The apparatus of claim 1, wherein said catalyst comprises one of a precious metal and an oxide.

6. The apparatus of claim 5, wherein said precious metal is selected from the group consisting of platinum, rhodium and gold.

7. The apparatus of claim 5, wherein said oxide of the catalyst is selected from the group consisting of manganese oxide, cobalt oxide and tin oxide.

* * * * *